(12) United States Patent
Yamazaki et al.

(10) Patent No.: US 7,764,991 B2
(45) Date of Patent: Jul. 27, 2010

(54) SYSTEM FOR DISPLAYING QUANTITIES OF BONE, WATER AND/OR MUSCLE OF BODY

(75) Inventors: Iwao Yamazaki, Tokyo (JP); Akitsugu Yamazaki, Tokyo (JP)

(73) Assignee: Ya-Man Ltd., Tokyo (JP)

( * ) Notice: Subject to any disclaimer, the term of this patent is extended or adjusted under 35 U.S.C. 154(b) by 0 days.

(21) Appl. No.: 10/517,490

(22) PCT Filed: Jun. 9, 2003

(86) PCT No.: PCT/JP03/07302

§ 371 (c)(1),
(2), (4) Date: Dec. 10, 2004

(87) PCT Pub. No.: WO03/105688

PCT Pub. Date: Dec. 24, 2003

(65) Prior Publication Data

US 2005/0177060 A1    Aug. 11, 2005

(30) Foreign Application Priority Data

Jun. 12, 2002 (JP) ............................. 2002-171928
Mar. 7, 2003 (JP) ............................. 2003-062347
Apr. 10, 2003 (JP) ............................. 2003-106928

(51) Int. Cl.
*A61B 5/05* (2006.01)
(52) U.S. Cl. ..................................... 600/547
(58) Field of Classification Search ............. 600/547
See application file for complete search history.

(56) References Cited

U.S. PATENT DOCUMENTS 2,842,135 A * 7/1958 Browner ..................... 607/3

(Continued)

FOREIGN PATENT DOCUMENTS

EP          0 998 875 A1    10/2000

(Continued)

OTHER PUBLICATIONS

Japanese Official Action, dated Nov. 9, 2004, for Japanese Patent Application No. 2003-106928, and English-language translation thereof.

(Continued)

*Primary Examiner*—Max Hindenburg
*Assistant Examiner*—Jeffrey G Hoekstra
(74) *Attorney, Agent, or Firm*—Finnegan, Henderson, Farabow, Garrett & Dunner, L.L.P.

(57) ABSTRACT

A display of the quantities of bone, water and/or muscle and a pulse health instrument in which the weight of bone or the weight rate of bone, the quantity of water and/or the quantity of muscle are measured and displayed to serve for sound diet and health management. Body fat rate is calculated by measuring the body impedance, quantity of bone, weight of bone, weight rate of bone, quantity of water and/or quantity of muscle are calculated based on the body fat rate and personal information inputted from a user, e.g. sex, age, height, body weight, length around wrist, length around ankle, and the like, and the results are displayed at a display section 105. Furthermore, the type of quantity of bone based on the correlation between the weight rate of bone and the body weight is judged and displayed in the matrix display region 111 of the display section 105.

5 Claims, 15 Drawing Sheets

U.S. PATENT DOCUMENTS

| | | | | |
|---|---|---|---|---|
| 2,995,132 | A * | 8/1961 | Browner | 607/72 |
| 5,579,782 | A * | 12/1996 | Masuo | 600/547 |
| 5,720,296 | A * | 2/1998 | Cha | 600/554 |
| 5,817,031 | A * | 10/1998 | Masuo et al. | 600/547 |
| 5,913,836 | A * | 6/1999 | Groux | 601/21 |
| 6,188,925 | B1 * | 2/2001 | Kawanishi et al. | 600/547 |
| 6,292,690 | B1 * | 9/2001 | Petrucelli et al. | 600/547 |
| 6,321,112 | B1 * | 11/2001 | Masuo | 600/547 |
| 6,393,317 | B1 * | 5/2002 | Fukuda et al. | 600/547 |
| 6,456,873 | B1 * | 9/2002 | Inoue et al. | 600/547 |
| 6,539,310 | B2 * | 3/2003 | Shimomura | 702/19 |
| 6,643,542 | B1 * | 11/2003 | Kawanishi | 600/547 |
| 7,008,350 | B1 * | 3/2006 | Yamazaki et al. | 482/8 |
| 2002/0049546 | A1 * | 4/2002 | Shimomura | 702/19 |
| 2002/0091420 | A1 * | 7/2002 | Minogue et al. | 607/48 |
| 2004/0077968 | A1 * | 4/2004 | Simond et al. | 600/547 |
| 2005/0059902 | A1 * | 3/2005 | Itagaki | 600/547 |

FOREIGN PATENT DOCUMENTS

| | | |
|---|---|---|
| EP | 1 201 187 A1 | 5/2001 |
| EP | 1 222 895 A1 | 7/2002 |
| EP | 1 132 046 A1 | 9/2009 |
| JP | 7-75625 | 3/1995 |
| JP | 2726197 | 5/1997 |
| JP | 11-113870 * | 4/1999 |
| JP | 11-123182 * | 5/1999 |
| JP | 11-128195 | 5/1999 |
| JP | 11-188016 | 7/1999 |
| JP | 11-318845 | 11/1999 |
| JP | 2000-41966 | 2/2000 |
| JP | 2000-51370 | 2/2000 |
| JP | 2000-051370 * | 2/2000 |
| JP | 2000-107148 | 4/2000 |
| JP | 2001-190514 | 7/2001 |
| JP | 2002-112976 | 4/2002 |
| JP | 2002-291912 | 10/2002 |
| WO | WO 99/58054 | 11/1999 |
| WO | WO 99/60925 | 12/1999 |
| WO | WO 01/15600 A1 | 3/2001 |
| WO | WO 02/11616 A1 | 2/2002 |

OTHER PUBLICATIONS

International Preliminary Examination Report, dated Mar. 17, 2004, issued in PCT Application No. PCT/JP2003/07302.

InBody 3.0 Body Composition Analyzer. Catalog. BioSpace Co., Ltd., 1999.

European Search Report dated May 15, 2009.

* cited by examiner bone somatotype judgment men

| | age | height (cm) | weight (kg) | wrist (cm) | IMP | fat ratio (%) | weight except fat(%) | BCA (kg) | DXA (kg) |
|---|---|---|---|---|---|---|---|---|---|
| 1 | 51 | 165.0 | 56.0 | 16.6 | 806.0 | 24.7 | 42.2 | 1.95 | 1.64 |
| 2 | 57 | 162.0 | 53.0 | 16.0 | 717.0 | 15.8 | 44.6 | 2.06 | 1.53 |
| 3 | 23 | 171.0 | 62.0 | 15.2 | 716.0 | 25.5 | 46.2 | 2.09 | 2.48 |
| 4 | 50 | 157.0 | 62.0 | 16.0 | 660.0 | 24.4 | 46.9 | 2.14 | 2.50 |
| 5 | 26 | 175.0 | 60.0 | 16.4 | 738.0 | 17.5 | 49.5 | 2.26 | 2.36 |
| 6 | 41 | 160.0 | 75.0 | 17.6 | 649.0 | 33.5 | 49.9 | 2.26 | 2.12 |
| 7 | 26 | 177.0 | 63.0 | 17.0 | 773.0 | 20.0 | 50.4 | 2.31 | 2.36 |
| 8 | 23 | 178.0 | 63.0 | 16.4 | 743.0 | 19.8 | 50.5 | 2.28 | 2.26 |
| 9 | 45 | 171.5 | 64.0 | 16.0 | 705.0 | 20.7 | 50.8 | 2.27 | 2.14 |
| 10 | 59 | 163.0 | 63.0 | 16.2 | 595.0 | 17.3 | 52.1 | 2.32 | 2.24 |
| 11 | 40 | 175.0 | 63.0 | 15.2 | 695.0 | 16.7 | 52.5 | 2.27 | 2.42 |
| 12 | 63 | 170.0 | 63.0 | 17.4 | 634.0 | 15.8 | 53.0 | 2.40 | 2.37 |
| 13 | 27 | 175.0 | 68.0 | 16.4 | 689.0 | 20.7 | 53.9 | 2.37 | 2.24 |
| 14 | 45 | 174.0 | 64.0 | 16.8 | 643.0 | 15.5 | 54.1 | 2.39 | 2.14 |
| 15 | 48 | 177.0 | 65.0 | 16.8 | 675.0 | 15.6 | 54.9 | 2.41 | 2.29 |
| 16 | 25 | 170.0 | 80.0 | 17.6 | 650.0 | 29.8 | 56.2 | 2.43 | 2.83 |
| 17 | 38 | 171.0 | 77.0 | 17.4 | 583.0 | 22.0 | 60.1 | 2.55 | 2.89 |
| 18 | 30 | 177.0 | 120.0 | 20.0 | 518.0 | 35.1 | 77.9 | 2.86 | 2.82 | women

| | age | height (cm) | weight (kg) | wrist (cm) | IMP | fat ratio (%) | weight except fat(%) | BCA (kg) | DXA (kg) |
|---|---|---|---|---|---|---|---|---|---|
| 1 | 25 | 160.0 | 48.0 | 13.8 | 975.0 | 26.4 | 35.3 | 1.85 | 1.92 |
| 2 | 47 | 151.0 | 50.0 | 14.8 | 796.0 | 25.3 | 37.4 | 1.96 | 1.80 |
| 3 | 52 | 161.0 | 58.0 | 14.0 | 917.0 | 30.7 | 40.2 | 1.82 | 1.73 |
| 4 | 27 | 166.0 | 54.0 | 17.0 | 858.0 | 24.6 | 40.7 | 2.08 | 2.40 |
| 5 | 55 | 156.0 | 54.0 | 15.6 | 725.0 | 24.0 | 41.0 | 2.00 | 2.04 |
| 6 | 59 | 155.0 | 57.0 | 13.8 | 735.0 | 24.8 | 42.9 | 1.95 | 1.96 |
| 7 | 25 | 162.0 | 58.0 | 14.8 | 877.0 | 23.8 | 44.2 | 2.09 | 2.06 |

SYSTEM FOR DISPLAYING QUANTITIES OF BONE, WATER AND/OR MUSCLE OF BODY

CROSS REFERENCE TO RELATED APPLICATION

This application is a national phase application based on PCT/JP03/07302, filed Jun. 9, 2003, the content of which is incorporated herein by reference.

TECHNICAL FIELD

The present invention relates to a display equipment for measuring and displaying the features or characteristics of a body including the quantities of the bone, the water content and/or the muscular amount of the body.

BACKGROUND ART

The human body contains essentially water content including blood, muscular, bones and fat therein. A sound diet is to reduce fat ratio in the body. However, the diet to control merely the meal could reduce the body fatness, but further would reduce the muscular and/or bone amounts of the body, so that the total weight could be reduced but the fat ratio would not be reduced significantly. Further, that would reduce the basal metabolism so as to result in a risky physical condition easy to raise the fat ratio of the body. Then, the target of the diet is to make the physical condition in which the basal metabolism would be improved to raise efficiently the fat consumption rate.

An aerobic exercise would consume the body fat amount present in the muscular as a fuel by oxygen, in which the basal metabolism would raise so as to reduce the fat ratio of the body. This is ideal measure for diet.

Recently, there have been provided various types of pulse health equipment which provides expectation of body fatness reduction effects which can be expected as well as in the aerobic exercise, by applying pulse currents from outside into the human body, to stimulate electrically the muscular of the body so as to shrink the muscular thereby giving the reduction of the fat ratio in the body as well as the effect of aerobic exercise. This kind of pulse health equipment can provide the body with effective shrinkage exercise of the muscular more effectively than the result of actual exercise, which would raise a basic metabolism of the body.

It is important to control and/or manage the diet amount (the intake calorie of food). However, it is very difficult for the individual to estimate accurately the appropriate calorie intake, because it depends on the weight, age, sex and the daily exercise and the other parameters and there is no available calculation formula to give theoretical good result. The aerobic exercise together with diet restriction would reduce the amounts of the muscular and bone of the exercising people so as to cause their worn out state. Then, the exercise and/or diet would affect their body.

It is the object of the present-invention to provide a display equipment for measuring and displaying the amounts of the bone, water and muscular of the body which respectively constitutes to the body, so as to indicate those amounts, so that the user could refer to those values for giving sound diet and health management.

DISCLOSURE OF THE INVENTION

It is an object of the present invention to provide a display equipment to represent a bone amount, water content and/or muscular amount of the body, which is provided with a plurality of electrodes to establish electric contact with the body, a means for measuring the impedance between respective sites of the body by supplying respectively currents for the measurement into the body through each of the plurality of electrodes, an entering means for entering the personal information of the user such as his weight, means for estimating approximate values of the bone weight on the basis of the measured impedance by the measuring means, and the personal information as entered, and the output means for representing the resulting approximate values of the bone weight as calculated.

In accordance with the present invention, the inventive display equipment can enable to give the approximate values of the bone weight, water content and/or muscular weight of the user, and further to provide the information such as the changes or shift of the bone weight, water content and/or muscular amount for the user to control the diet or the food amount for effective dieting, and for keeping his healthy body.

The personal information provided from the user may include the weight of the body, male or female, his age, his height, the length around wrist, length around ankle and the like. The weight data can be entered directly from the weight scales. The ratio of bone weight as actually measured per the whole weight excluding the fat weight has somehow correlation to sex, age, height, weight, length around wrist, length around ankle. Those correlation can be derived from the statistical calculation, and then, using the bone measurement, the approximation of the bone weight can be finely done.

The means of estimating the approximate values will calculate the approximate values of the water content and muscular weight of the user other than the bone weight. The resulting values are represented on the display for reference of proceeding diet process, and selecting the appropriate diet exercise. Upon reviewing in approximation the bone amount as well as the water content and muscular quantity of the body, his health condition can be precisely managed for the sound diet. The displayed approximate values can be reported by voice at the same time. Alternately, the reporting can be done only by the voice.

Further, preferably, the inventive display equipment can provided with a memory for recording the resulting values as calculated by the estimating means and a display means for displaying the values as measured at the last time as memorized in the memory. Therefore, the user can review and compare the values of the bone amounts, water contents and muscular quantity as measured at the last time and this time, so that the user can easily understand the tendency of the changes in such values.

Therefore, in accordance with one of the preferable embodiment of the present invention a weight scales can be preferably combined with the inventive display equipment to indicate the bone weight, water content and/or muscular weight.

More preferably, the inventive equipment can have a means for judging the somatotypes as judged from the correlation between the approximate values and the body weight, as well as display means for representing the somatotype as judged by the judging means. Then, the user can review the condition of the body, such as how thin his body becomes, and how healthy he is now, by representing the somatotypes depending the corrections of the weight with the bone weight as well as the water content and the muscular weight of his body.

Further, the inventive display device can have a means for feeding treatment pulses to the human body through the plurality of the electrodes so as to treat the body.

The inventive display equipment can be provided with an exercise machine such as an aero-bicycle and a step meter for counting the number of the steps when the user walks, for the user to refer to the approximate values such as the bone rate, water content and/or the muscular rate of his body.

BEST MODE FOR CARRYING OUT THE INVENTION

The embodiment of the invention will be explained in reference to the drawings.

Figure 1:
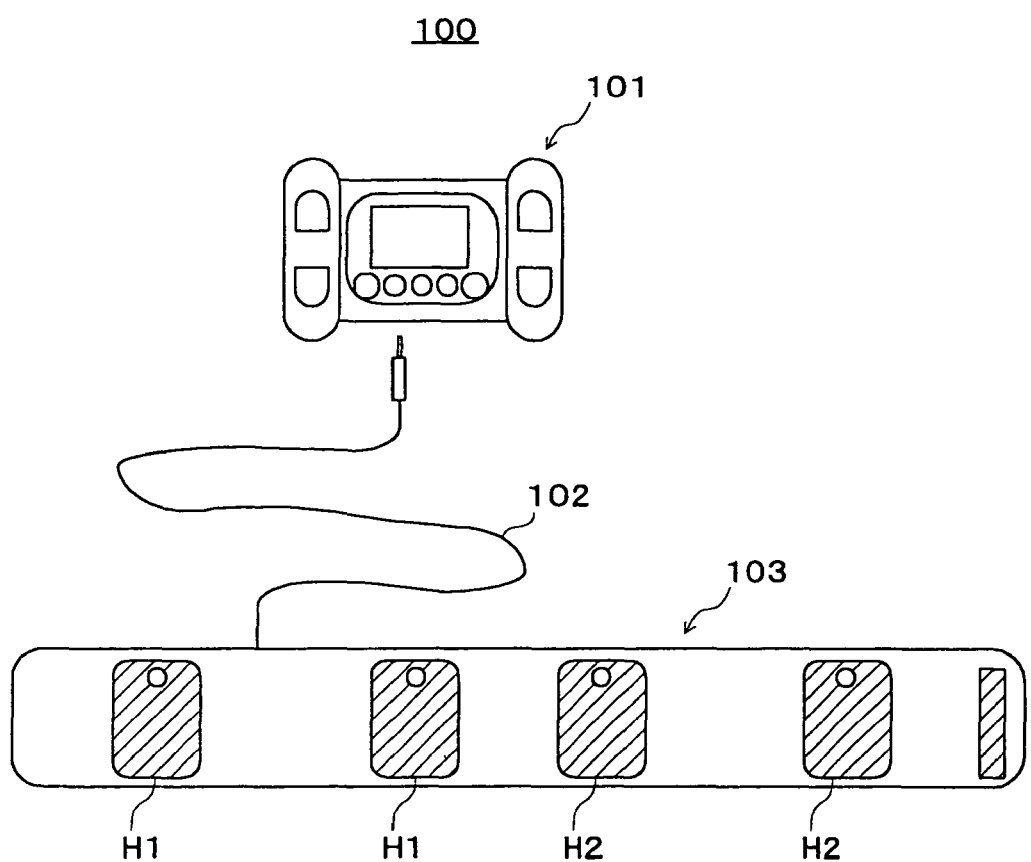
FIG. 1 is a view illustrating schematically the whole structure of the inventive display equipment for displaying the bone ratio, water content and/or the muscular ratio of the body.

FIG. 1 illustrates wholly a pulse health equipment 100 in combination with an electrode belt 103 to display the bone amount, water content and/or muscular ratio on the handy display 101. As shown in this drawing, this pulse health equipment 100 has a handy type pulse health body 101 and the electrode belt 103 to connect thereto through a cable 102.

Figure 2:
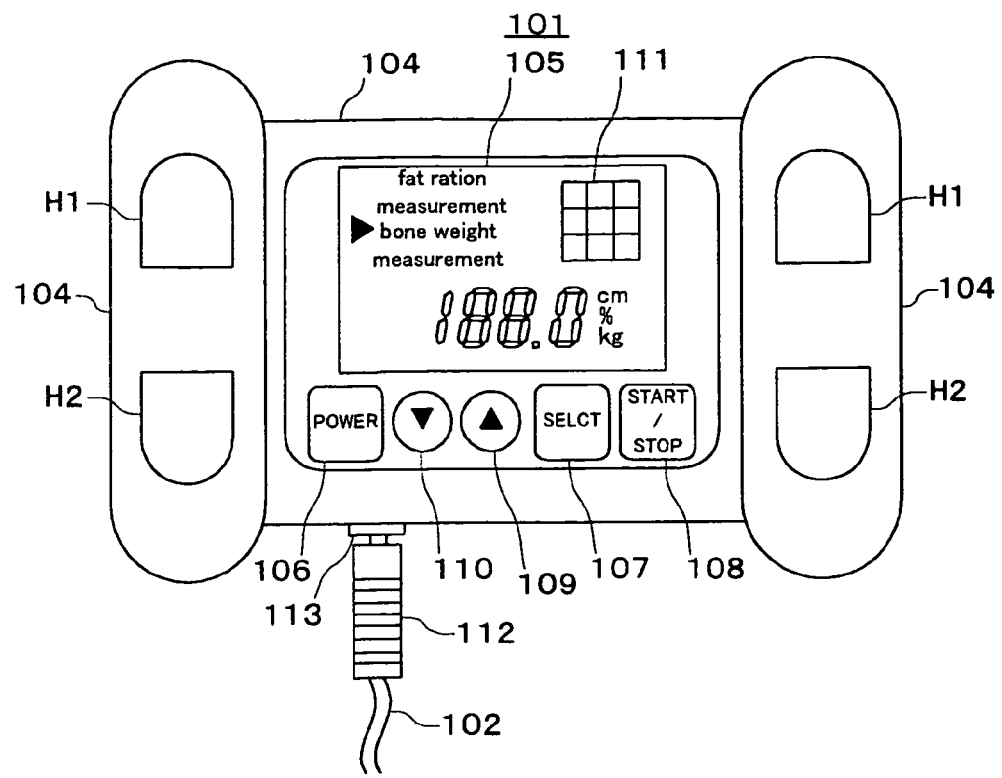
FIG. 2 is a view illustrating schematically a front view of equipment of display and pulse equipment in combination in accordance with the present invention.

FIG. 2 shows a front view of the pulse health equipment body 101. In reference to FIG. 2, the pulse health equipment 101 has a pair of handles 104 at its both ends; in which there are provided the potential loading electrodes H1 and the detecting electrodes H2. At the central portion of the equipment, that is, between the pair of the handles 104, there are provided the display and operation elements 114, in which the display 105 such as composed of LCD is provided on the upper side of the display-operation elements 114. At the lower portion of the display 105, there are provided a source switch bottom 106 to turn on and off the source, and a selection button 107 to select the functions such as body fat ratio measurement, bone ratio measurement and treatment, a start and stop bottom 108 to initiate and finish the functions of the equipment, and a up key 109 and down key 110 to change the personal information such as the male or female of the user, the age of the same, the height of the same, the weight of the same, the length around the hand of the same, the length around the foot, the strength, frequency of the pulse current to load, and the time of the treatment to be applied to the user. For example, the strength of the pulse current can be selected from the literal expressions such as "rubbing", "softening", "pushing", "beating" and "crumpling up" in order of strength from weakest to stronger, and the user can select the strength by using the up/down keys 109 and 110.

The display 105 has a matrix pattern scope 111 to indicate the personal information from the user, the selected function which the user has selected, its operation condition, the results of the measurement of values such as the fat ratio, and bone ratio, as well as the judgment of the somatotype of the user which has been, selected on the basis of the correlation between the fat ratio with the weight of the user, and the somatotype which has been selected from the correlation between the bone amount and the weight of the user. The term of "bone amount" is referred to "bone weight" or "bone ratio" of the user, in which the "bone ratio" means a ratio of bone weight to the whole weight of the user. The "bone amount" can be referred to "bone volume".

The pulse health equipment 101 has a connector 113 to which a connecting jack 112 of a connecting cable 102 should be inserted for an electrode belt 103.

Figure 3:
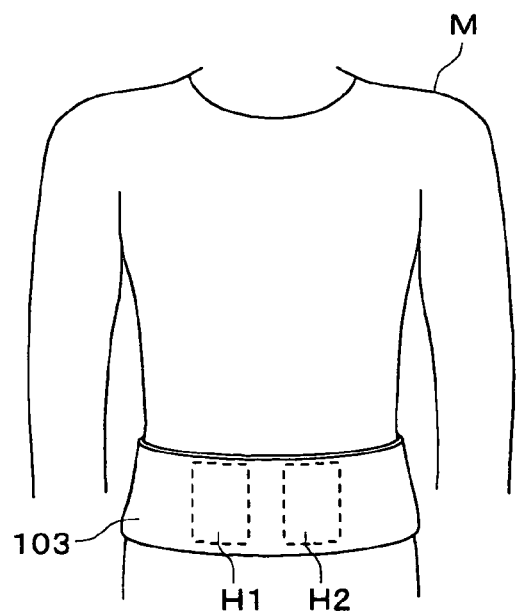
FIG. 3 is a view illustrating schematically an embodiment of the electrode belt of the equipment of FIG. 1 as used by the user.

The electrode belt 103 is shown in FIG. 3 and can be used with wrapping on the body (abdomen) of the user M. As shown in FIG. 1, the electrode belt 103 has four plane electrodes H1 and H2. Those plane electrodes H1 and H2 correspond respectively to the four sites of the right and left, front and rear positions of the abdomen of the user M, among them, the pair electrodes H1 of the left side, front and rear sites are potential applying electrodes, and the pair electrodes H2 of the right side, front and rear sites are the detecting electrodes. Further, the plane electrodes H1 and H2 are electrically connected to the pulse health equipment, 101 through the cable 102.

Those four electrodes H1 and H2 of the electrode belt 103 can be made from a coating of electrically conducting carbon ink as applied on the surface of the soft urethane resin sheet, and further can be made from aluminum foil applied on the surface of a soft insulating strip, or from a strip of conductive rubber or silicon.

Figure 4:
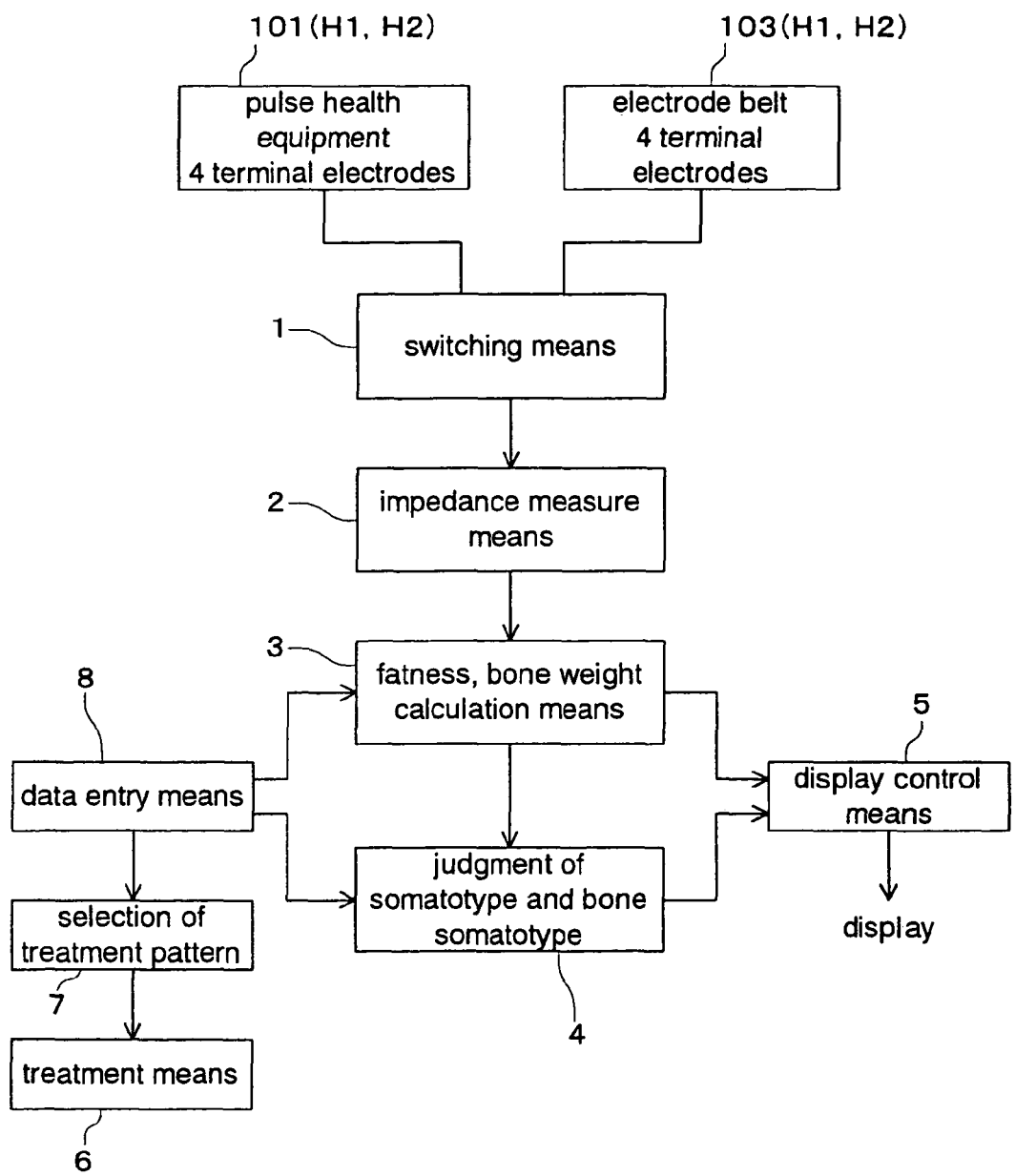
FIG. 4 shows a functional block diagram for the equipment of FIG. 1.

FIG. 4 shows a block diagram to illustrate the functional structure of the inventive pulse health equipment 100, in which a switching means 1, an impedance measuring means 2; a means 3 for calculating the fat ratio and bone ratio, a means 3 for judging the somatotype and bone somatotype, a means 5 for operating the display, a means 6 for treatment, a means 7 for selecting the treatment mode and a means 8 for input of the data.

The switching means 1 is to switch the connecting combination of each of the electrodes H1 and H2 of the pulse health equipment 101 and the electrode belt 103. There are provided at least the following combinations of the electrodes H1 and H2 to be connected.

(1) The combination to measure the impedance between both hands of the user, that is, to connect the potential loading electrode H1 and the detecting electrode H2 of the pulse health equipment 101;

(2) The combination to measure the impedance of the abdomen of the user, i.e. to connect the potential loading electrode H1 and the detecting electrode H2 of the electrode belt 103;

(3) The combination to measure the impedance between the hand and the abdomen of the user, i.e. to connect either electrode of the pulse health equipment and either electrode of the electrode belt 103.

The switching means 1 is to switch sequentially the connecting combinations (1), (2) and (3). That is, it is to switch the connection sequentially for the measurement of the impedance between both hand, of the abdomen, and between the hand and the abdomen.

The means 2 for measuring the impedance is to apply a given voltage (e.g. sign curve alternating current voltage of 50 kHz) to the potential electrode H1, and to detect the voltage of the detecting electrode H2 so that the impedance between both hands, of the abdomen and between the hand and the abdomen can be measured.

The means 3 for estimating the body fatness and bone ratio is to calculate the body fatness of each portion of the body, and the average value thereof, as well as the bone weight and bone ratio of the user, on the basis of the impedance as measured on each of between both hands, abdomen and between abdomen and hands of the body by the impedance measurement means 2 and the personal information as input by the input means 8.

The means 4 for judging the somatotype depending on the correlation between the fatness and the weight of the user on the basis of the fatness as calculated by the means 3, and the personal information as input by the data entering means 8, and further, judging the bone somatotype of the user depending on the correlation between the bone weight and the weight of the body on the basis of the bone weight ratio as calculated by the means 4 and the personal information as entered by the data input means 8.

The display control means 5 is to represent the value of the fat ratio as calculated by the means 3, on the display picture 105, and to represent the somatotype as judged by the judging means 4, on the matrix display area 111 of the display 105.

The display control means 5 is to represent the bone weight value as calculated by the means 3 on the display area 105, and further to represent the bone somatotype as judged by the means 4 on the basis of the correlation of the bone weight and the body weight.

The treatment means 6 is to treat the human body via a plurality of electrodes mounted on the pulse health equipment 101 and the electrode belt 103 to stimulate electrically the human body.

The treatment selecting means 7 is to select the kind of the electric pulse applications in accordance with the user's command, and to apply the selected treatment on the body of the user.

The operation for the measurement of the fatness and bone amount of the body by the pulse health equipment 101 will be explained as follows.

1. Firstly, wrap the electrode belt around the portion such as waist or abdomen of the user to equip.

2. Select the functions of fatness measurement by using a function select button 107 of the pulse health equipment 101.

3. Enter the personal information of the user by using an up key 109 and down key 110. At the same time, enter the personal information such as male or female, age, height and weight of the user for the measurement of the fatness and bone weight.

4. Get stick the grips 104 at the left and right ends of the equipment 101 to both hands of the user, and then push the start/stop button 108 in such contact state.

5. Detect the impedance respectively between both hands, abdomen and hands.

6. Calculate the fatness of each position of the body, and the whole fatness of the user on the basis of the impedance of each position as measured between hands, abdomen and hands, and the personal information as entered by the entering means 8.

7. Display digitally the values of the fatness at each position of the body, and the whole fatness (e.g. the average of the fatness of all positions).

8. Judge and represent in the matrix area 111 of the display 105, the somatotype of the user on the basis of the correlation between the body fatness and the body weight, which is derived from the fatness as calculated by the means 3, and the personal information of the user, 9. Select the function for the measurement of the bone weight by using the select button 107 of the pulse health equipment 101.

10. Enter the personal information necessary to measure the bone weight by using the up key 109 and the down key 110.

11. Push the start/stop bottom 108.

12. Estimate the bone weight, bone ration of the user on the basis of the fatness as calculated and the personal information as entered.

Figure 9A:
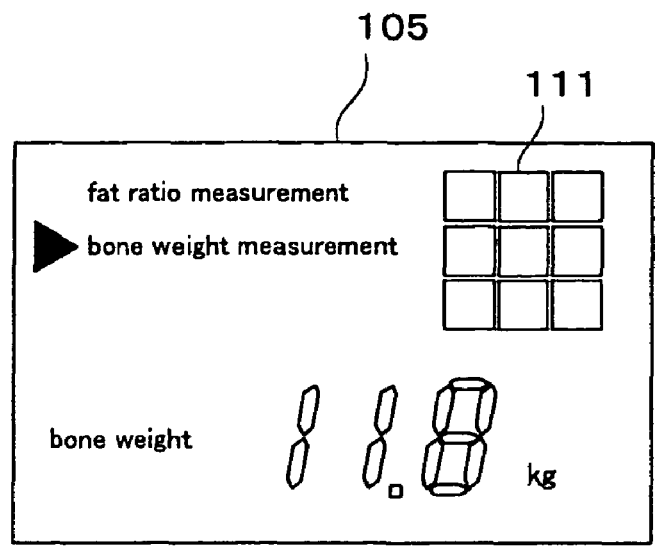
FIGS. 9A and 9B are a view illustrating schematically one embodiment of the display equipment for representing respectively the results of the measurement of the bone amount and the bone ratio as detected in accordance with the present invention.
Figure 9B:
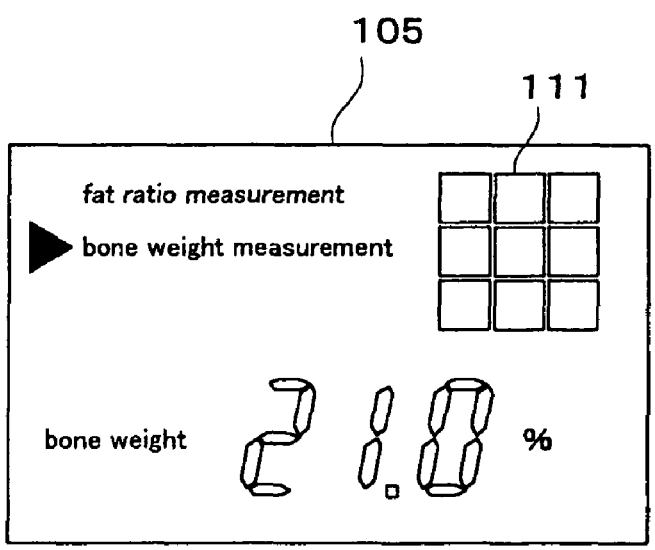

13. Display (represent) the results such as the estimated bone weight and bone ratio, as shown in FIGS. 9A and 9B.

14. Judge and represent on the matrix display area 111 of the display panel 105 the somatotype of the bone amount on the basis of the correlation of the bone weight with the body weight as calculated based on the bone ratio by the means 3, and the personal information entered by the data entering means 8.

Figure 5:
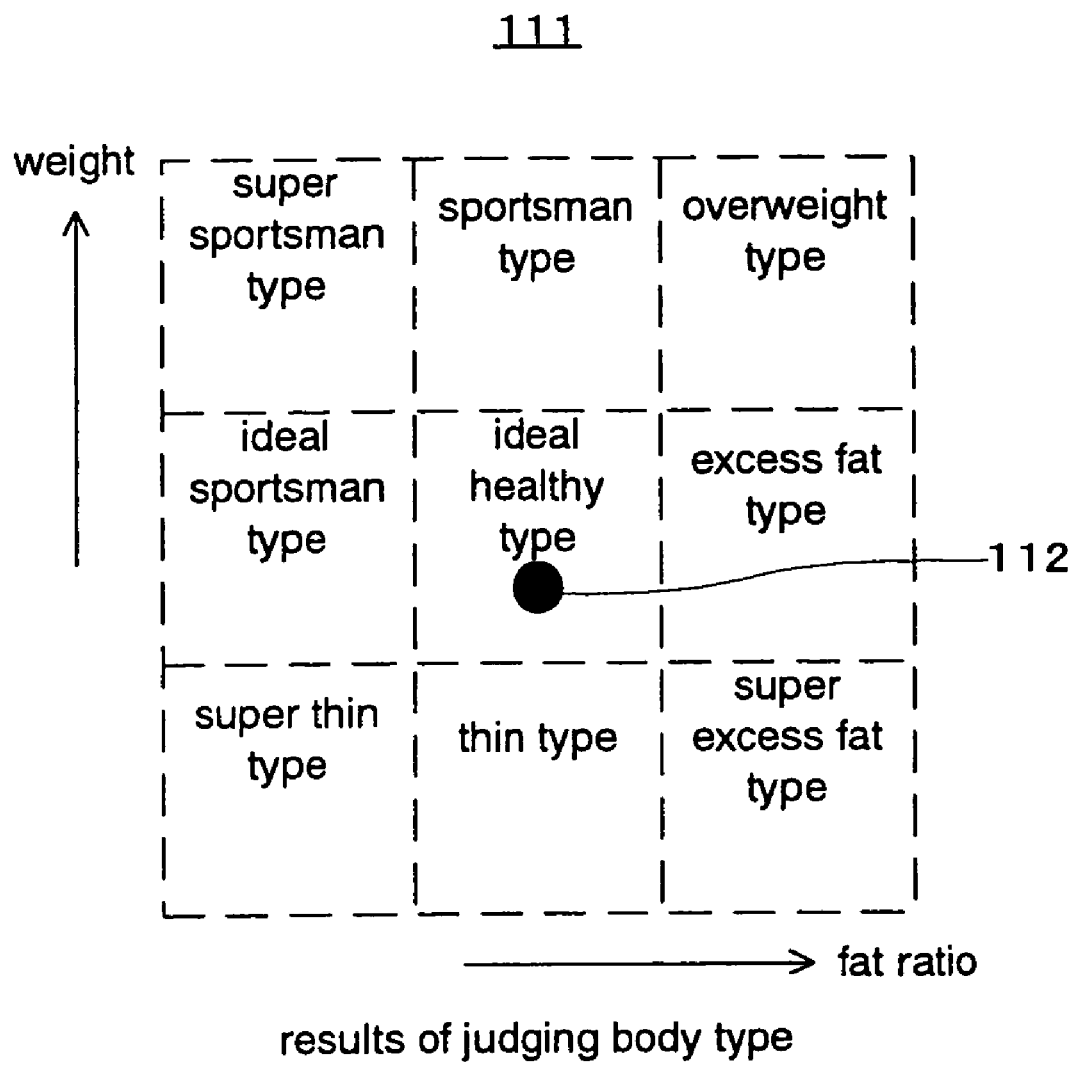
FIG. 5 is a view illustrating schematically the display representing the result of the judgment of the somatotype.

FIG. 5 shows a picture to illustrate the somatotypes on the matrix display scope 111, and further the bone somatotypes can be represented upon judging on the basis of the correlation between the bone amount and the weight of the user on the same matrix area.

Figure 6:
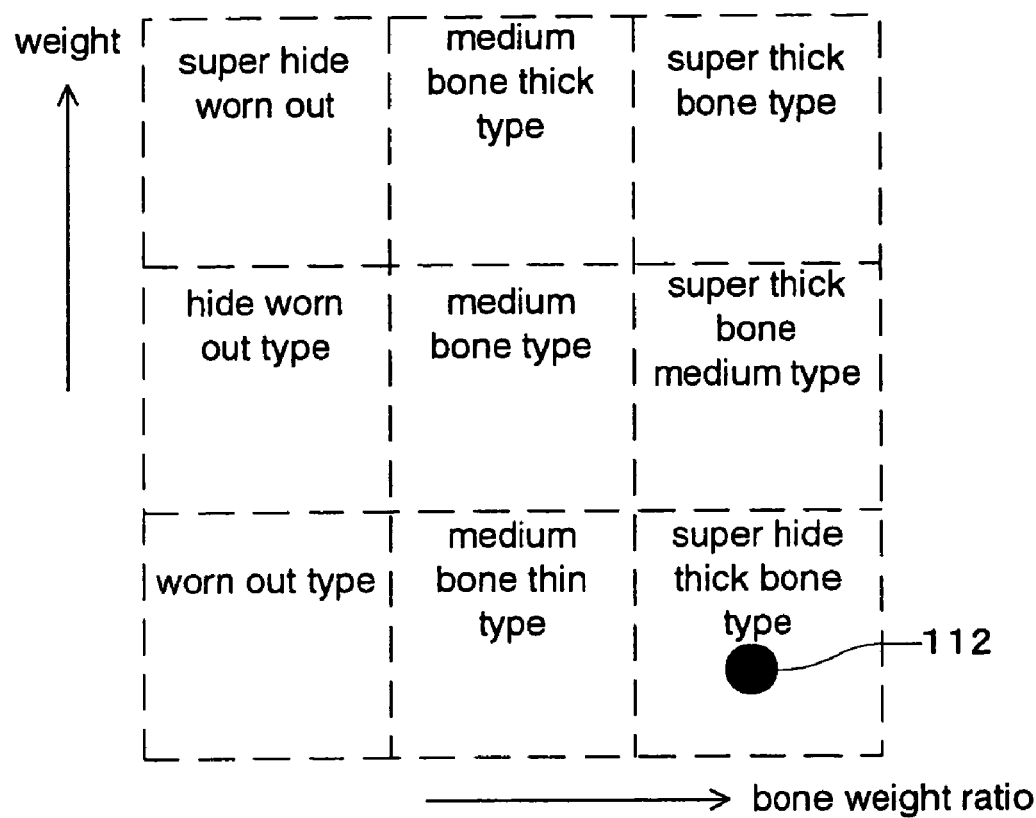
FIG. 6 is a view illustrating schematically the display embodiment for representing as a result of the bone amount the somatotype as judged in accordance with the present invention.

FIG. 5 shows a picture of matrix area 111 representing the somatotype, and FIG. 6 shows a picture of matrix area 11 representing the bone somatotypes judged on the basis of the correlation of the bone weight and the body weight.

As shown in the FIG. 5, the matrix display area 111 is divided into 9 sections D1, D2 . . . D9 in form of 3×3 in line and column. Each section D1, D2, . . . D9 can show a dot 115 on and off turning, in which the dot on and off represents the somatotype of the user, as well as the bone somatotype of the user as classified on the correlation of the bone weight and the body weight.

The letters (explanation) to be shown in each of the sections of the matrix area 111 which indicate the somatotypes or the bone somatotypes can be alternated by switching on indicating the bone somatotypes or the somatotypes depending on the selection of the bone somatotype or the somatotype. For example, the somatotype as judged in FIG. 5 is shown as "ideally healthy somatotype" by the on-off turning dot, on the other hand, the somatotype as judged in. FIG. 6 is shown as "super large-boned somatotype" by the on-off turning dot.

The judgment of the body somatotype would be done depending on the correlation between the fatness and the body weight as follows.

The means 4 of judging the body somatotype and bone somatotype of the user will recognize first which rank or level the body weight of the user should be classified to on the basis of the personal information such as sex, age, height and weight, as well as what rank or level the fatness of the user should be classified to on the basis of the fat ratio of the user as estimated by the means 3 of calculating the fatness and the bone weight. The rank of the body weight will be arranged along with the vertical axis of the matrix area 111 in which the medium sections show that the weight is ideal or medium. On the hand, the rank of the fatness will be arranged along with the horizontal axis of the matrix area 111 in which the medium sections evidence that the fatness is in the ideal range.

The ideal weight would be calculated on the basis of the following formula: (height−100)*0.9*0.91 wherein the unit of the height is in cm, and the unit of the weight is in kg. The ideal range of weight is (0.9~1.1)*the ideal weight. The ideal fat ratio is 17 to 24% for female; and 14 to 20% for male. The ranks of the weight and height will be classified by using those ideal weight, and fatness as a criterion (the medium range).

Each of the ranks for the body somatotype and bone somatotype is classified by the somatotype judging means 4, and the result as classified is reported to the display control means 5. The display means 5 will select one of the matrix display sections 111 with a dot turning off and on indication at the selected section.

The judgment of the bone somatotype will be done on the basis of the correlation between the bone weight and the body weight as follows.

The means 4 for judging the bone somatotype will judge the rank or level of the bone weight content as calculated by the means 3.

The way for calculating the bone weight by the fatness and bone weight estimating means 3 will explained as follows.

If the fat ratio is estimated on the basis of the measured impedance and the personal information, the body weight except of the fat weight can be estimated by subtracting the fat weight from the whole weight as entered as the personal information. Then, the bone weight ratio to the weight except of the fat weight has a certain correlation with the age and the sex, and therefore, such correlation can be derived statistically. For example, generally the ratio of the bone per the whole weight of male will be higher than that of female, and that will gradually decrease from the certain age, with age rising. Therefore, the approximate bone weight can be estimated by such determined correlation depending on the age and sex.

The ratio of the bone weight per the weight excluding the fat weight may be determined by either of parameters of the age and the sex, or alternatively by both parameters of the age and the sex. Further, the height of the user can be added as a third parameter.

For example, the height and the length around wrist and length around ankle, which are relevant to the diameter or thickness of the bone and can be readily measured, can be effectively used as a parameter for the precise estimation of the bone weight in approximation.

The calculation of the bone weight will be explained by using as a parameter, the length around wrist and length around ankle and the height.

The approximate values t of the diameters of the bones of the arm and the leg are calculated according to the equation (1) wherein the sex (Sx), age (Ag), height (H), the length around the wrist (R) and length around the ankle (An), the whole weight (W) are entered as the personal information, the fat ratio in average (Fp) has been calculated as above discussed. Alternatively, the length around knee, and length around elbow can be used in place of the length around wrist and length around ankle.

$$t = R + An - (a \times Fp) \quad (1)$$

wherein a is a constant which is predetermined by the sex (Sx), age (Ag), height (H).

The bone volume Bv can be estimated from the resulting approximate value t of the diameter t of the bone.

$$Bv = H \times t \times b \quad (2)$$

wherein b is a constant which is predetermined by the sex Sx and age Ag.

Then, the bone weight (Bw) will be estimated by the following equation.

$$Bw = D \times Bv \quad (3)$$

wherein D is a bone density which is predetermined by the sex (Sx) and age (Ag).

Finally, the bone ratio (Bp) is estimated from the bone weight (Bw) and body weight (W) by the following equation (4)

$$Bp = Bw/W \quad (4).$$

The method for calculation of the bone weight should not be limited to the above-discussed way. The other available method can be used.

The means 4 for judgment of the body somatotype and the bone somatotype will judge the level of rank of the bone weight and/or ratio as calculated by the means 3 for estimating the fat ratio, bone weight of the body, and the resulting ranks of bone weight and body weight are transferred into the display operating means 5. Then, the dot located in the corresponding section of the matrix area 111 shows on and off so as to represent the bone somatotype of the user, and thereby the users being enable to recognize his bone somatotype and to manage his diet and exercise plan.

Then, the treatments with pulse currents are explained as follows.

The pulse health equipment 100 can be operated to switch the parameters such as the frequency of the output pulse to be applied and the voltage to be applied in accordance with the users' instructions so that the treatment patterns can be readily selected and changed (Treatment selection means 7).

The patterns for the treatments can be classified into the following two categories; the toning in which the pulse current with low frequency of 5 to 10 Hz stimulates the deeper area of the body so as to move the bone flames thereby accelerating the flow of the blood, and to give the message to the body; and the drainage in which the pulse current with higher frequency of 20 to 100 Hz stimulates the surface area of the body so as to move the muscular of the surface area of the body, thereby stimulating the flow of the lymph, and to remove dropsy in the surface of the body.

Further, the pulse health equipment 100 can be arranged to have many kinds of treatments which are classified in the frequency much divided, and further to enable selecting readily the treatment among many kinds.

Further, the inventive display equipment can automatically select the appropriate kind of the treatment among such many kinds of the treatment, according to the resulting judgment of the bone somatotype on the basis of the correlation between the fat ratio and the body weight, or between the bone weight and the body weight.

The pulse voltage (treatment) patterns to be applied can be selected from the species of "drainage" or "toning". Among the species of "drainage" or "toning", there are "special drainage" and "special toning" both of which alter cyclically the pulse voltage to be applied so as to stimulate the body by such altering pulse voltages in which the pulse voltages might be made by time-dividing between the electrodes on which the voltage is applied, so called "time-dividing drainage" and "time dividing toning". The inventive equipment may have the selection function among such many kinds of the treatment.

The circuits to be used for the measurement of the impedance among the portions of the body, as well as for application of the predetermined patterns of the pulses will be explained as follows.

Figure 7:
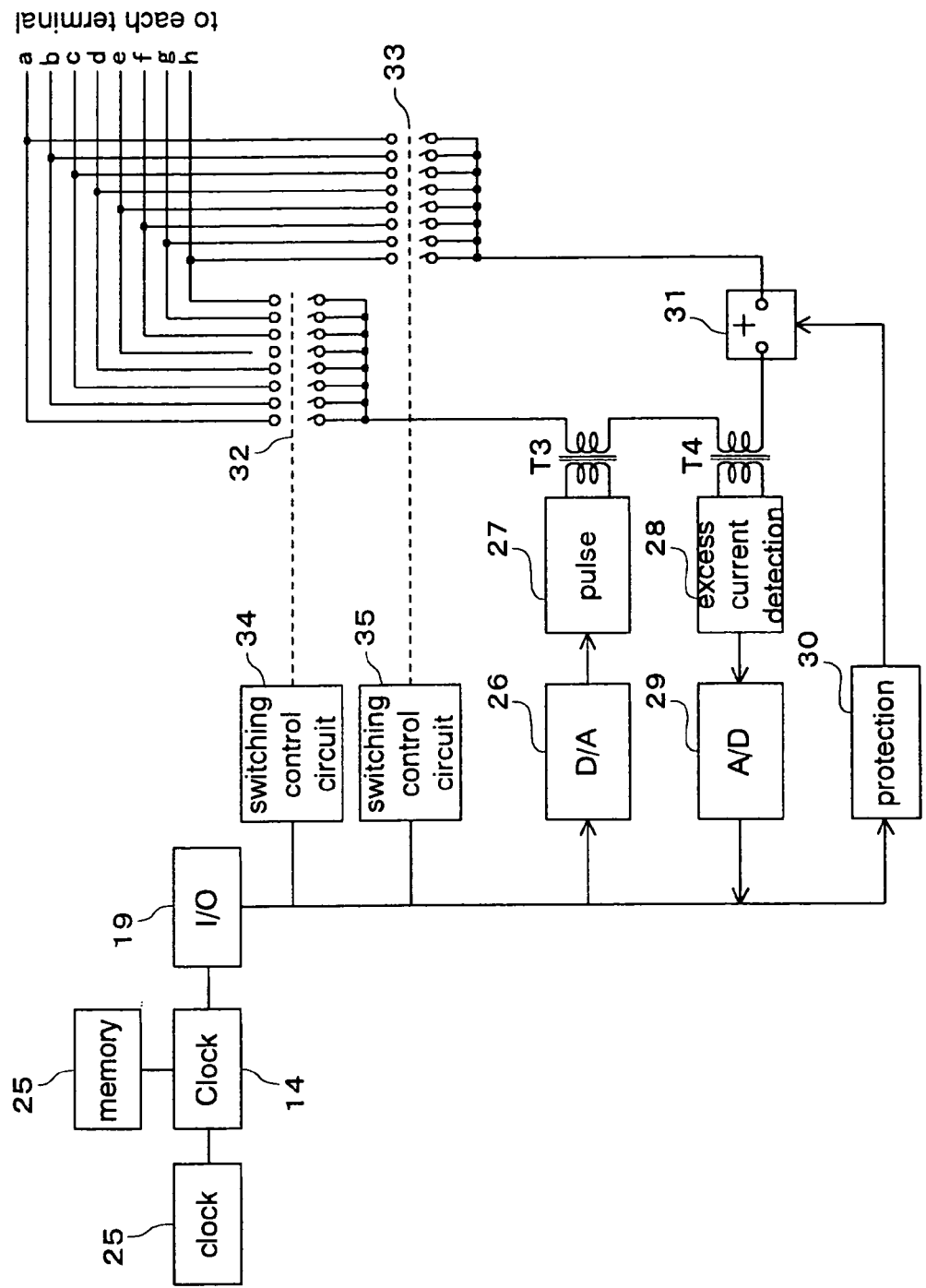
FIG. 7 is a view illustrating schematically one embodiment of the circuit for the treatment means in the pulse health equipment in accordance with the present invention.
Figure 8:
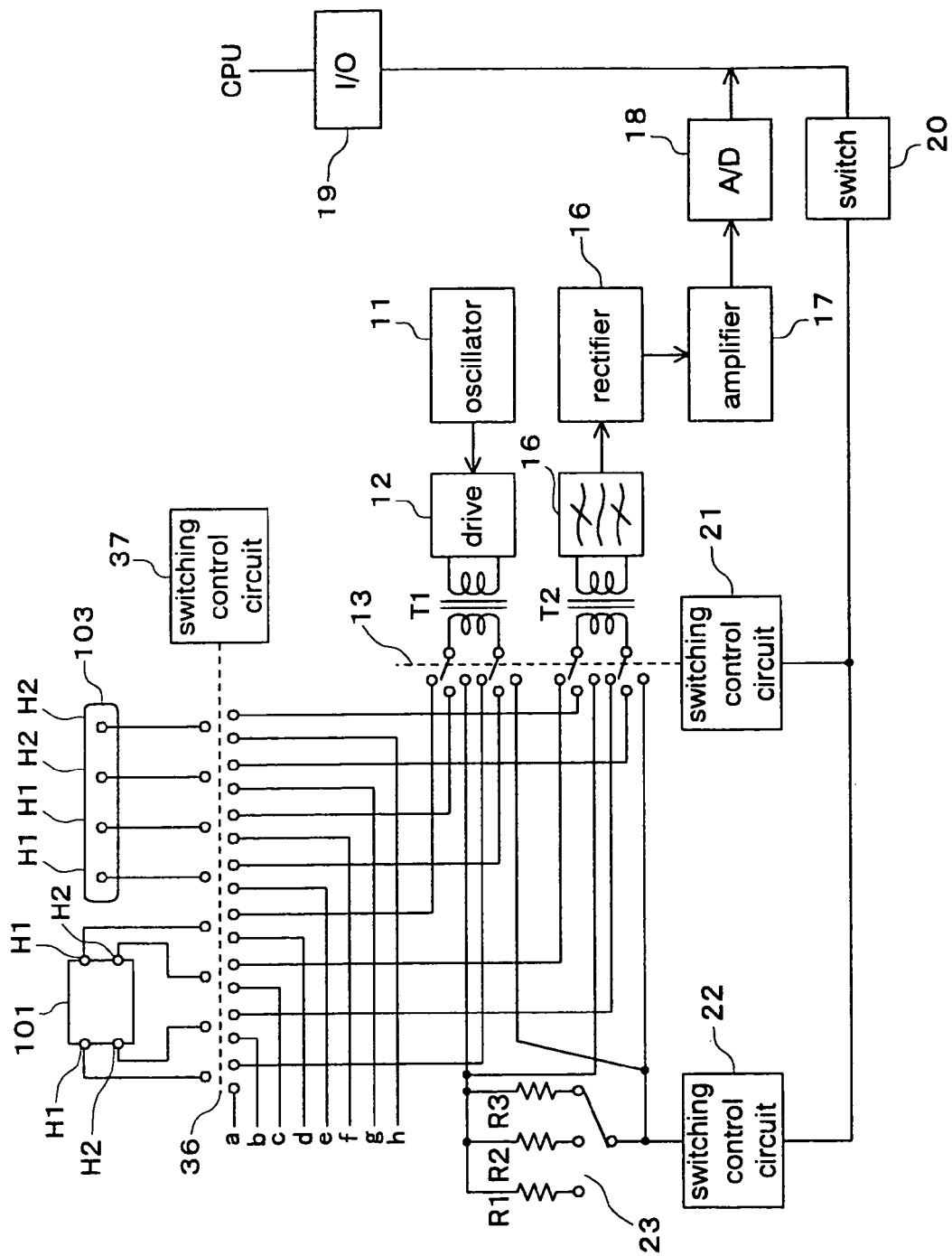
FIG. 8 is a view illustrating schematically one embodiment of the circuit for the measurement of the impedance in the pulse health equipment in accordance with the present invention.

FIGS. 7 and 8 shows respectively the compositions of the circuits. These generates an oscillation of voltage in the sinusoidal altering curve, which supplies this oscillation output to a driving circuit 12, a transformation converter T1, a pulse health equipment 101 and an input electrodes H1 and H2 of the electrode belt 103 via a selecting switch 13.

The measurement of the body impedance is carried out under such state that the left handle 104 of the pulse health equipment 101 is grasped by the hand of the user for the fingers of the user to get touch the supply electrode H1 and the detect electrode H2, and at the same time, the belt 103 is to be wrapped around his waist. When the user pushes the start/stop button 108 under such state, the switch 13 will turn the circuit for measurement on, charging and the detecting voltage occurs in the pulse health equipment 101, on the detecting electrode H2 of the belt 103.

The selecting switch 13 is operated to control the selection and the timing of switching so that the respective measurement of the impedance between both hands, the impedance of the abdomen, and the impedance between abdomen and hand can be enabled. That is, a switching control signal from CPU will enter into the I/O interface 19, a switching unit 20, and then the switching control circuit 21 will change the switch 13 on the basis of the switching control signal.

The altering voltage as generated at a detecting electrode H2 will be transformed into a continuous current through a switch 13, a transformer T2, a band pass filter 15, a rectifier circuit 16, and an amplifier 17, and then, wave shape regulated, level-adjusted, off-set adjusted, and then transformed into a digital signal with A/D transformer 36, and put into CPU 14 through an I/O interface 19. Thereby, the impedance between the left and right hands, among the positions around the waist, and between the hand and the position around the waist can be separately measured.

Before measuring the impedance, measurement errors due to the aging and temperature change of the measuring circuits should be corrected by operating to correct the outputs of the detecting circuit features as follows.

The relationship of the three parameters of body impedance Z (the impedance between left and right hands, among the position around the waist, and between the hand and the position around the waist) with the detected altering voltage V as detected by the detect circuit can be referred to the regression line equation: $Z = k \cdot V + C_0$. The given altering voltage which is the same as to that in which the body impedance is measured is charged between the both terminals of the circuit of three dummy resistances R1, R2 and R3 as known, and the altering voltage A as generated between the both terminals of the circuit of the three dummy resistances R1, R2 and R3 is detected to determine the relative constant k of the regression line and the fixed constant C0.

In order to correct the output feature of this detect circuit, the CPU will switch a switch 23 through an I/O interface circuit 19, a switching unit 20 and a switching control circuit 22, and then, the connection with the secondary terminals of a transformer T1 and the secondary terminals of a transformer T2 will switch from the electrode H2 of the detect side to the dummy resistances, R1 R2 and R3, and at the same time change a switch 13 through the switching control circuit 21 into the three dummy resistances R1, R2 and R3.

The CPU 14 will determine a frequency demultiplication of a clock pulse of a standard clock generator 25 corresponding to a treatment purpose as selected by a treatment pattern selector 7. Then, the CPU will supply the digital trigger signals demultiplied by the frequency demultiplication to a pulse generator 27 through an I/O interface 19 and D/A converter 26. The pulse generator 27 will generate a frequency and a voltage pulse corresponding to the selected treatment purpose, and supply to a primary side of the transformer T3.

The secondary terminals of transformer T3 connect serially a primary coil of a transformer T4, and the secondary coil of the transformer T4 connects a current detecting circuit 28 for detecting the excess current. The current as detected by the current detecting circuit 28 will be put into the CPU 14 through an A/D converter 29 and I/D interface 14. The CPU 14 will break down the cutout switch 31 by a current protection circuit 31, when the current value exceeds the standard level.

The secondary side of the transformer T1 is connected respectively to the pulse health equipment 101 through a switch 32 and a switch 33 comprising a photo-coupler, and a supply electrode H1 and detect electrode H2 of the belt 103. The switch 32 and switch 33 are under the control of CPU 14, so as to change or select the supply of the treatment pulse to that between the both hands, the positions of the body and between the hand and the abdomen by using the switching circuit 34 and switching circuit 35.

Further, switching between the impedance measurement and the treatment can be done by switching a switch 36 with a switching circuit 37.

The pattern for the treatment to be applied can be selected in accordance with the body somatotype and bone somatotype of the user and further, the user can select the pattern to be applied on the basis of his preference or favorite.

In accordance with the embodiment of the pulse health equipments, as described the bone amount such as the bone weight and bone ratio can be measured (determined) in approximation. Therefore, the diet can be adjusted during the dieting period so as to keep his health sound so that the respective health condition can enable to be managed in the sound and controlled condition.

The second embodiment of the inventive display equipment will be explained. In this second embodiment, the display equipment can measure the approximate values of the bone weight, as well as water content and/or muscular weight in the approximation. Hereinafter, "bone weight" represents bone weight and bone weight ratio in the body, "body fatness" represents fat weight and fat ratio, and "water content of the body" represents the water content or weight in the body, and "muscular weight" represents muscular weight and muscular weight ratio in the body. All of the ratios are represented on the basis of the whole body weight. This second embodiment of the display equipment cam be combined with the pulse health equipment, but there is explained especially regarding the display function of the equipment.

Figure 10:
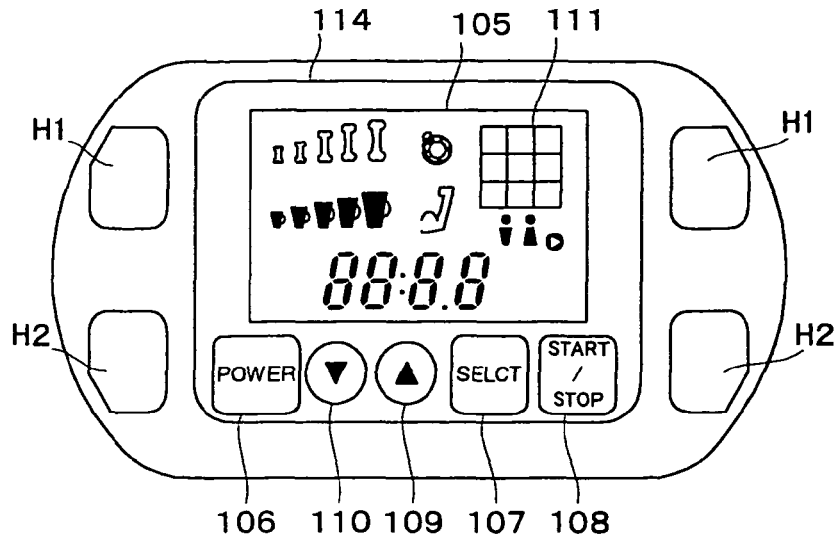
FIG. 10 is a front view illustrating schematically the second embodiment of the display representing in combination the bone amount, water content and/or the muscular ratio as detected in accordance with the present invention.

FIG. 10 illustrates schematically a front view of the display 100 of the second embodiment of the present invention.

As shown, there are provided respectively potential feed electrodes H1 and detecting electrodes H2 at the both sides of the display equipment. The potential electrode H1 and detecting electrode H2 of the left side are touched by the fingers of the left hand of the user, and then the potential electrode H1 and detecting electrode H2 of the right side are touched by the fingers of the right hand of the user. Between the left and right side electrodes, there is provided a display-operation portion 114 in which the display elements such as LCD are provided. At the lower portion of the display 105, there are provide a source button 106 to switch on and off the electric source, a function select button 107 to select the functions of the equipment such as measuring fat ratio, bone ratio, water content or muscular ratio of the body, a star/stop button 108 to start and stop the operation of the function, and up and down keys 109 and 110 to put in personal information such as the sex, age, height, weight, length around the waist and length around the ankle of the user.

Figure 11:
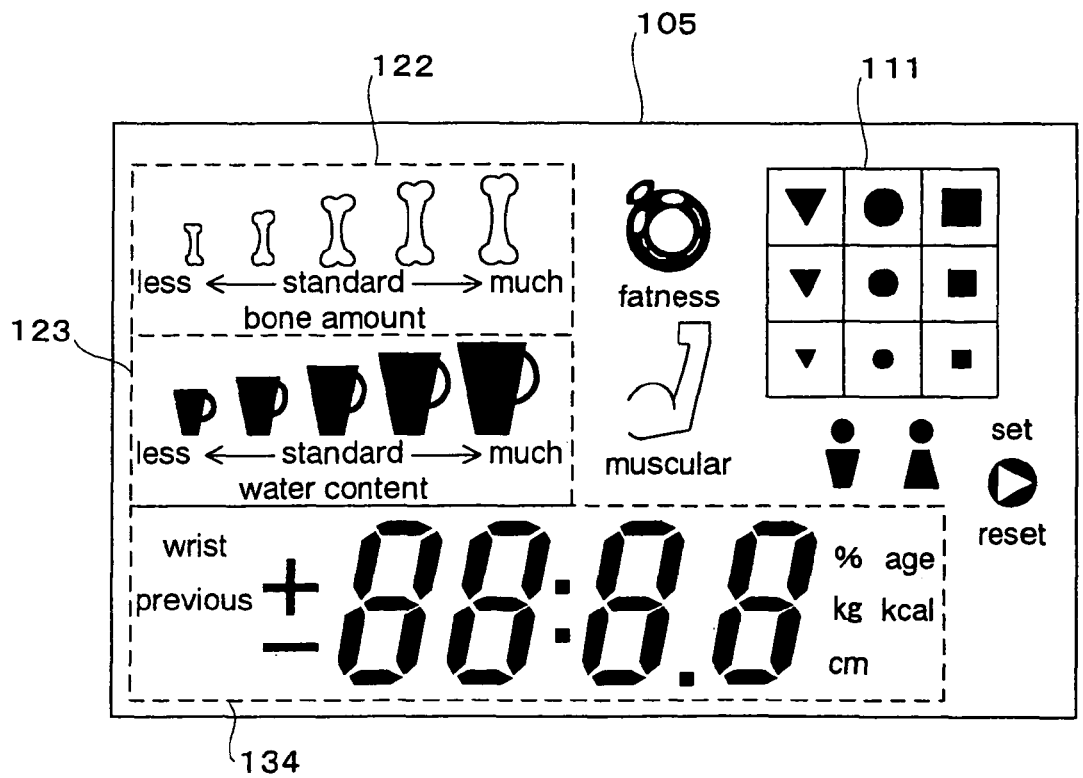
FIG. 11 is a view illustrating schematically the picture embodiment of the display of FIG. 1 representing the bone amount, water content and/or the muscular ratio.

FIG. 11 illustrates schematically the composition of the picture of the display 105. The picture of the display 105 comprises a scope range 134 to indicate numerical values such as the age, height, weight, length around the waist and length around the ankle of the user, the resulting fat ratio, bone ratio, water content and muscular ratio of the body of the user, and further the function and operation that the user has selected, a matrix scope range 111 to indicate the somatotype of the body of the user as judged on the basis of the correlation of the bone ratio with the weight of the user, the somatotype of the body of the user as judged on the basis of the correlation of the fat ratio with the weight of the user, the somatotype of the body of the user as judged on the basis of the correlation of the water content with the weight of the user, and the somatotype of the body of the user as judged on the basis of the correlation of the muscular ratio with the weight of the user, and the scope range 122 to indicate the bone amount by using the number of the bones shown in the picture, and the scope range 123 to indicate the water content by using the number of the buckets in the picture.

Figure 12:
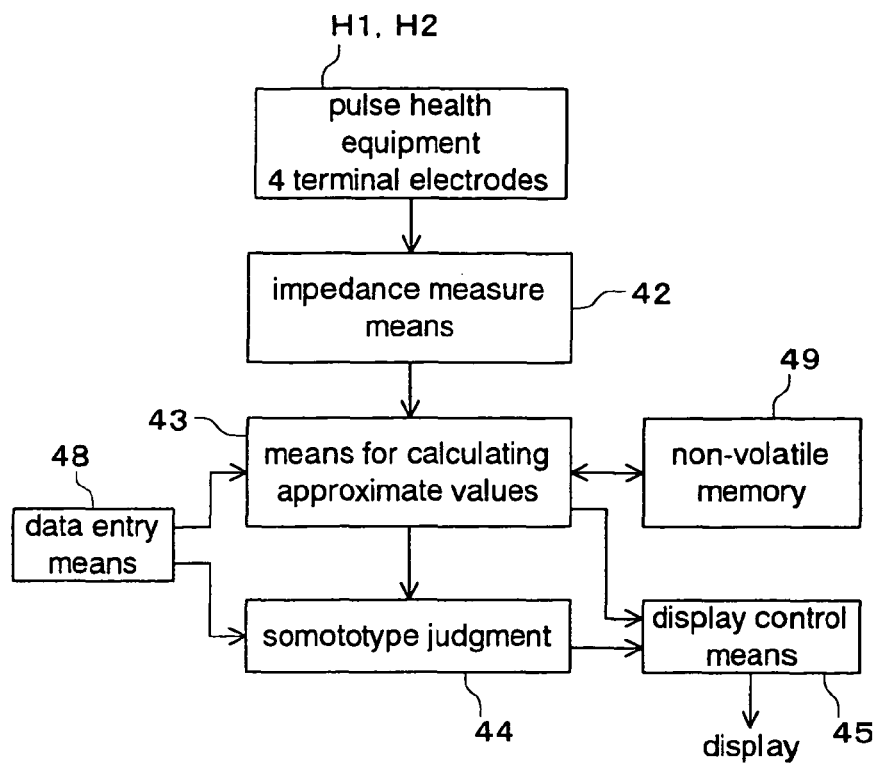
FIG. 12 is a view illustrating schematically the functional block diagram for the display 200 of FIG. 1 to represent the bone amount, water content and/or the muscular ratio.

FIG. 12 shows a functional block diagram of the display equipment 200.

As shown, this equipment 200 has an impedance measurement means 42, a means 43 for estimating the approximates of the fat ratio, bone ratio, water content and the muscular ratio of the body, a somatotype judgment means 44, a display operation means 45, a data entering means 48 and an non-volatile memory 49.

The impedance measurement means 42 is to apply the given potential for example sign curve alternating current voltage of 50 kHz) to the potential electrode H1, and to detect the potential of the detect electrode H2, and thereby to measure the impedance between the both electrodes.

The means 43 for estimating the approximates of the fat ratio, bone ratio, water content and the muscular ratio of the body is to estimate the approximates of the fat ratio, bone ratio, water content and the muscular ratio of the body on the basis of the measured impedance and the personal date of the user which have been put in.

The somatotype judgment means 44 is to proceed the judgment of the somatotypes as classified by the correlation of the fat weight ratio with the weight of the user, or that of the bone weight ratio with the weight of the user, or that of the water content with the weight of the user, or that of the muscle weight ratio with the weight of the user, on the basis of the results of the estimation by the means 43 on the body fat amount, bone weight, water content, muscle amount of the user, and further the personal information of the user.

The non-volatile memory 49 is to store measured data such as the fat weight, bone weight, water content and muscle weight as measured at the last time. The last data as stored in the non-volatile memory can be read only by the user, and further can be indicated on the display 105. Further, the measured data as stored in the non-volatile memory 49 can be renewed or rewritten automatically in the memory. Further, the data measured in the past several times can be stored in the memory, and then, the data as measured and stored in the past times can be processed so as to present graphically on the display the change or shift of the past times.

The display equipment 200 of the present invention will be explained as to how to measure and indicate the fat weight, bone weight, water content, and muscle weight of the body.

1. The personal information data such as the sex, age, height, weight, length around the wrist, length around the ankle of the user are put into the equipment by using the up key 109 and down key 110.

2. Just after pushing the start/stop button 108, the feed electrode H1 and detect electrode H2 at the left and right end of the display equipment 200 are adhered on the surfaces of the left and right thumbs of the user.

3. The impedance of the user are measured.

4. The means 43 for estimating the approximate values such as the fat ratio, bone weight, water content and muscle weight of the user will calculate those values on the basis of the measured impedance and the personal information.

5. The means 44 for judging the somatotype of the user will classify or judge the body somatotype of the user on the basis of the correlations of the weight respectively with the approximate values of the fat ratio, bone weight, water content and muscle weight which have been estimated by the means 43. The results of the calculation of the body fatness, bone weight, water content and muscular weight, and further the result of the judgment are stored in the memory.

6. The results of the measurements are read and represented on the display, when the user selects the result to be shown among the body fatness, bone weight, water content and muscular amount of the user.

Figure 13:
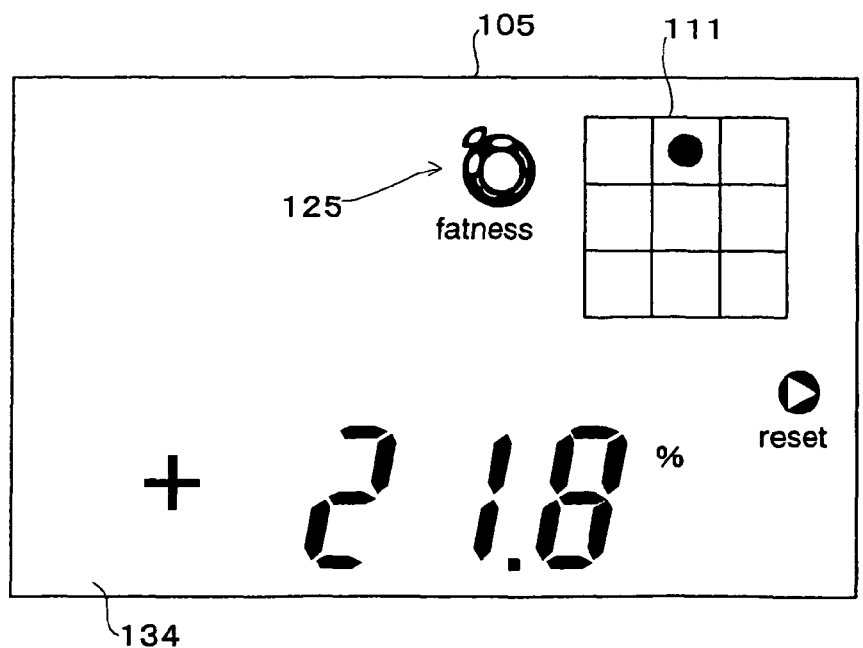
FIG. 13 is a view illustrating schematically one embodiment of the picture on the display representing one of the results of the measurement of the fat ratio as detected in accordance with the present invention.
Figure 14:
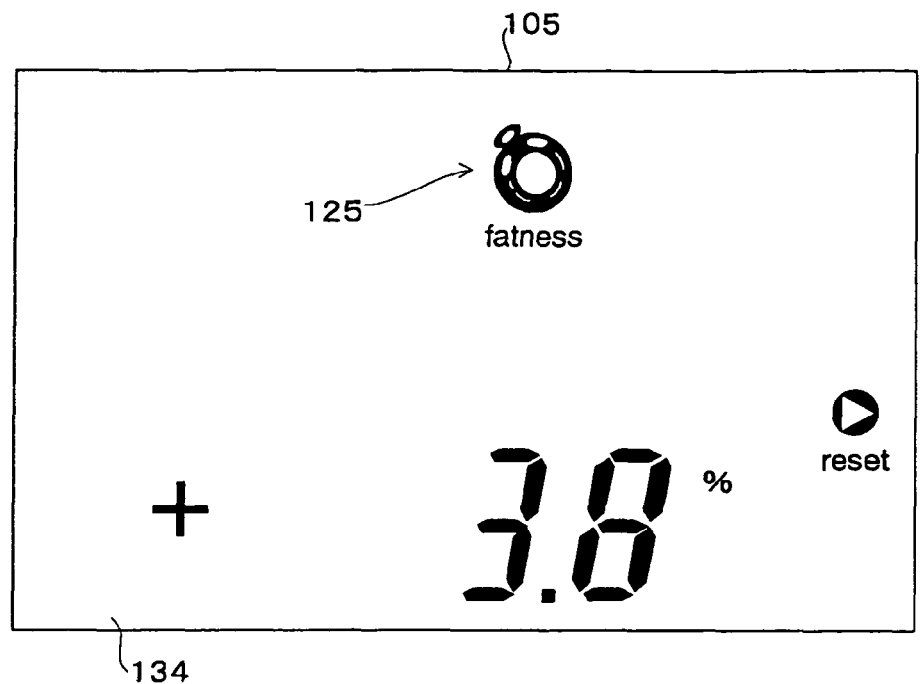
FIG. 14 is a view illustrating schematically one embodiment of the picture to represent one of the results of measurement of the body fat ratio and the difference from the ideal value.

FIG. 13 is a view of display face to present the result of the measurement of the fat ratio. The picture 125 is displayed together with the result of the measured fat ratio, and further the value of the fat ratio is displayed in the numeric representation area 134, as well as the somatotype as judged on the basis of the correlation of the fat ratio with the weight is shown at the same time. Then, just once pushing the up key 109, the difference between the ideal fat value and the actual fat value is shown in the numeric area 134 of the display 105, as shown in FIG. 14.

Figure 15:
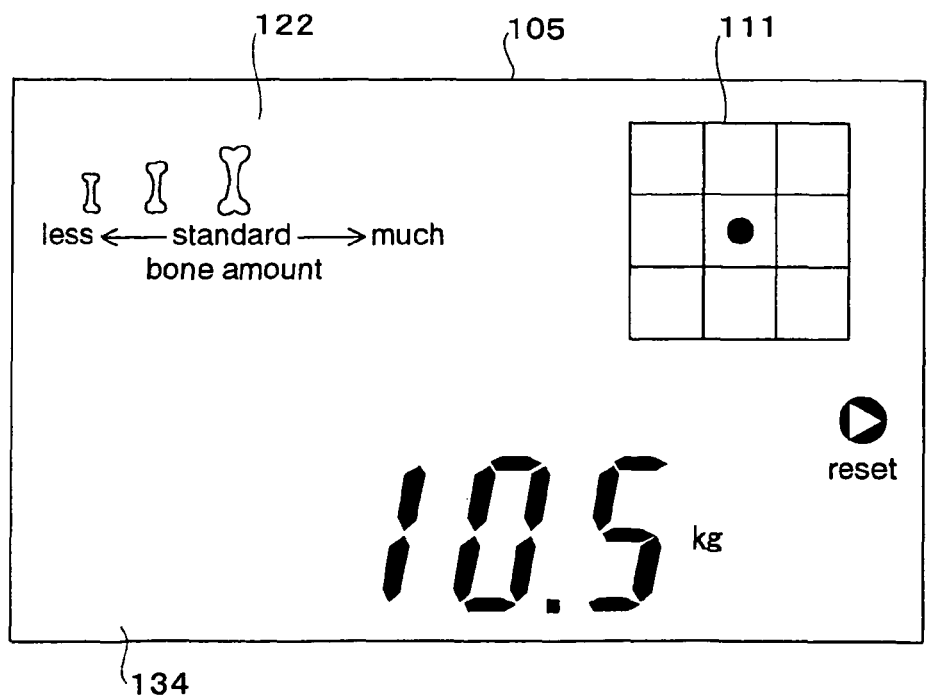
FIG. 15 is a view illustrating schematically another embodiment of the picture to represent one of the results of the bone measurement in accordance with the present invention.

FIG. 15 shows a picture representing the result of the measurement of the bone weight. The somatotype as determined on the basis of the correlation between the bone weight and the body weight is represented in the matrix area 111. Further, the rank representing the level of the bone weight as measured is shown in form of bone size in the area 122.

Figure 16:
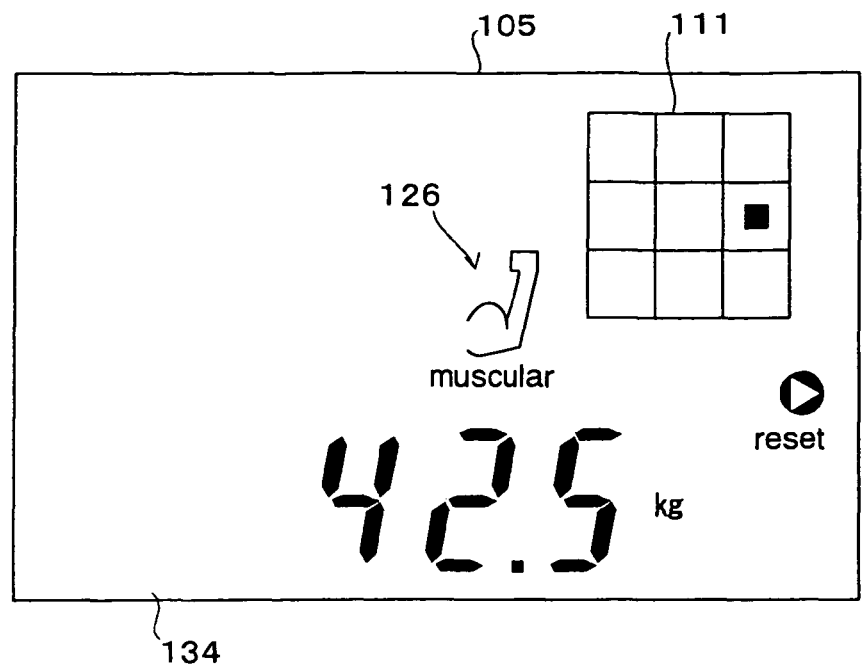
FIG. 16 is a view illustrating schematically another embodiment of the picture to represent one of the results of the muscular measurement in accordance with the present invention.

FIG. 16 shows a picture representing the result of the muscular weight as measured. In this pictures an arm as shown at 126 represents that this is the result of the muscular weight as measured, and the value of the muscular weight is shown in the numeral area 134, and then, the muscular somatotype as classified according to the correlation between the muscular weight and the body weight is shown in the matrix area 111.

Figure 17:
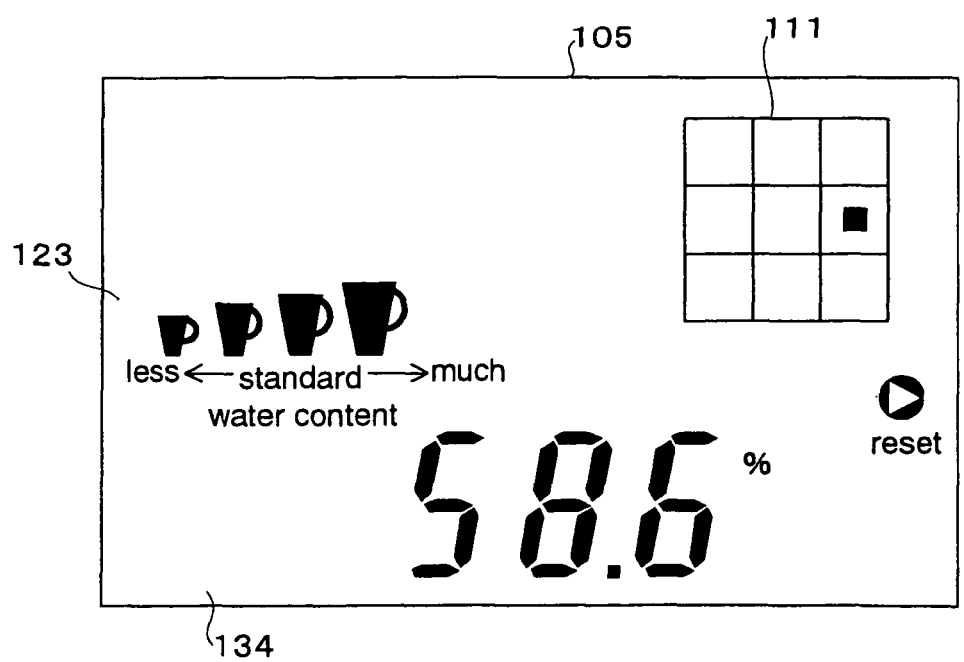
FIG. 17 is a view illustrating schematically another embodiment of the picture to represent one of the results regarding the water content as measured in accordance with the present invention.

FIG. 17 shows a view illustrating the picture to represent one of the results regarding the water content of the body as measured in accordance with the present invention. The value of the water content is shown in the numeric representation area 134 in percent unit, as well as the somatotype of the body as judged based on the correlation between the water content and the weight of the body. The rank of the water content is shown in the area 122 by using the number of cups in picture.

Figures 18, 19:
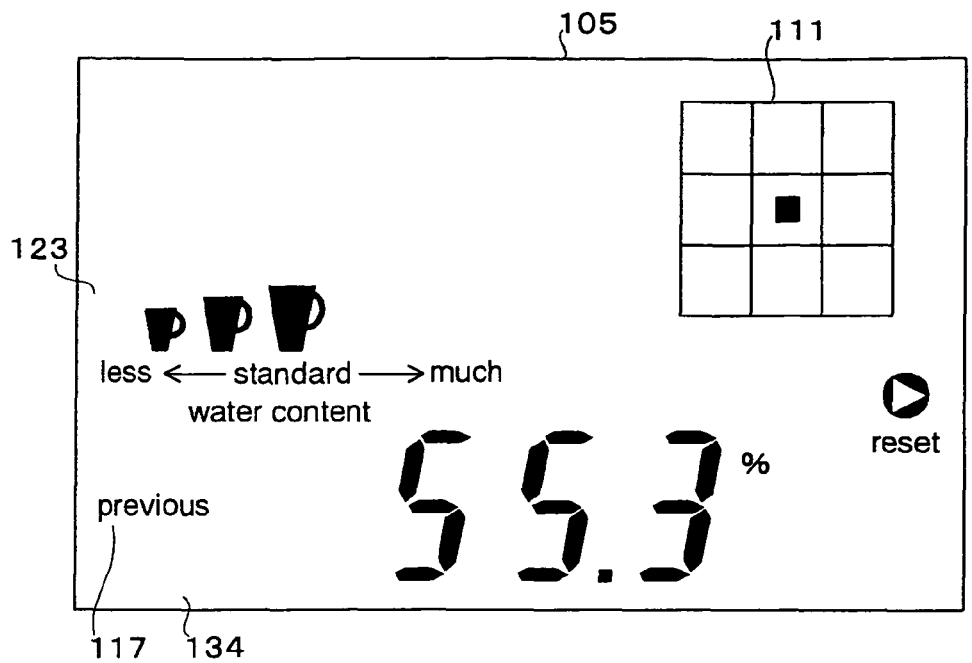
FIG. 18 is a view illustrating schematically an embodiment of the picture to represent one of the previous results regarding the water content as measured previously in accordance with the present invention.
FIG. 19 is a table illustrating the results of the bone measurement about the male group by using the second display of the present invention, in comparison with the result according to DXA method.

The display equipment 200 is provided with a non-volatile memory 49 to store the data as obtained at the last time for the measurement. The picture of FIG. 17 representing the present result can be changed into the picture of FIG. 18 representing the result of the last time as stored in the memory 49, by pushing the up key 109. The data as shown can be recognized by indicating "last time" in the letter 117 for the user. Then, the data as stored in the memory 49 will be rewritten as the new data after finishing the measurement.

Further, the difference in the measured data between the present time and the last time can be shown in the data representation picture.

Then, the concrete method of the measurement and representation of the fat amount, bone amount, water content and muscular amount of the body with the display equipment 200 will be explained as follows.

Whereas the fat ratio can be estimated on the impedance as measured and the personal information, the body weight excluding the fat weight can be calculated by subtracting the calculated fat weight from the whole body weight as entered as the personal information. The fat weight is a factor to affect much the body weight, and on the other hand, the other factors such as bone weight, water content and muscular weight depend on the conditions parameter such as sex, age, height and weight, but the dependency is lower than any of the body fat weight. Therefore, it is proposed that the ratios of the bone weight, water content and muscular weight per the whole weight except of the fat weight which have been respectively calculated by the statistical way can be used to determine the bone weight. That is, the multiplication of the whole weight excluding the fat weight with the bone ratio in average which has been statistically estimated will lead to the approximate bone weight of the user. Further, by the similar way, the multiplication of the whole weight excluding the fat weight with the water ratio in average which has been statistically estimated will lead to the approximate water content of the user, and further the multiplication of the whole weight excluding the fat weight with the muscular ratio in average which has been statistically estimated will lead to the approximate muscular weight of the user. Therefore, the resulting approximate values can be indicated as a result of the measurements, but in accordance with the present invention, the additional correction of the resulting values is carried out to give more precise values as follows.

The approximate values which have been estimated by the statistical average ratios will be further corrected by using the sex, age, height, whole weight, the length around the wrist and length around the ankle as the personal information, so as to give more precise values. For example, the statistic ratio in average of the bone weight to the whole weight except of the fat weight would be 0.215, and the statistic ratio in average of the water weight to the whole weight except of the fat weight would be 0.723, and then, those ratios are multiplied to the whole weight except the fat weight so as to give each of the resulting bone weight and water weight, and then, the correction constants determined accordance with the sex, age, height, whole weight, the length around the wrist and length around the ankle as the personal information is added so as to correct the results of the bone, water and muscular weights in approximation. The display equipment 100 can be provided with such correction function, for example, some software. Please note that the length around the wrist and length around the ankle might not be effective to the correction of the water weight of the body.

The body weight excluding the fat weight can be estimated by the sum of the bone weight, water content weight and muscular weight, and therefore, for example, first the bone weight and water content weight are calculated from the averages which are statistically, and then the resulting sum of the bone weight and water content weight is subtracted from the body weight excluding the fat weight so as to give the bone weight in approximation.

Herein, the "bone weight" means the weight of the bone composition in the human body, that is, the weight of the bone in the human body including water content contained in the bone composition. There is the other term of "bone salt amount" in this terminology. This term means the amount of mineral, i.e. calcium atom in the bone. Then, this bone salt amount might be estimated on the basis of the body weight excluding the fat weight.

In this case, there may be provided a certain coefficient classified on the level of the weight except of the fat weight. For example, the coefficient is 0.045 when the weight except of the fat weight ranges 40 to 45 kg. The weight except of the fat weight is multiplied by this coefficient so as to give the factor which might be used further to correct the estimated bone weight in view of the measured length around the wrist. The resulting corrected bone weight should be a precise measured value of the bone weight.

Figures 20, 21:
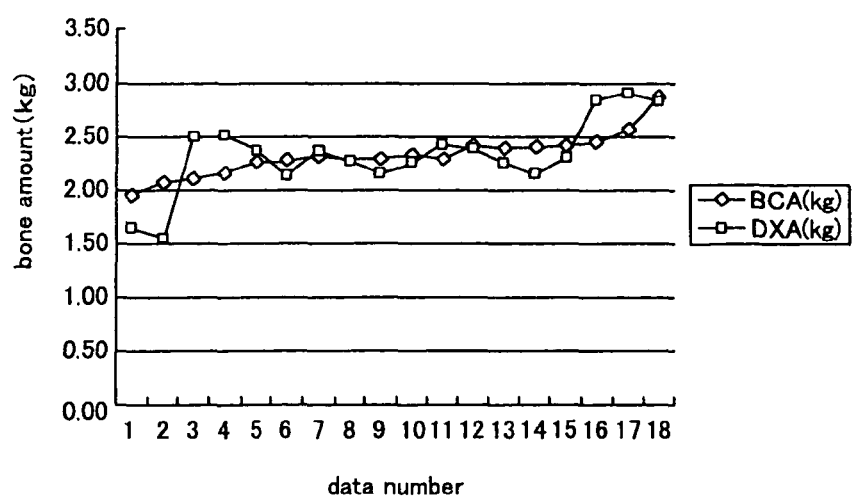
FIG. 20 is a table illustrating the results of the bone measurement about the female group by using the second display of the present invention, in comparison with the results as measured according to DXA method.
FIG. 21 is a view illustrating graphically the difference of the bone amounts as measured by BCA method and DXA method of FIG. 19.

The accuracy of the bone weight measurement is explained in reference to FIGS. 19 and 20, which show respectively the table showing the measurement result given by DXA method, respectively in regard to the male and female result of the bone weight measurement. Herein, IMP refers to the measurement impedance of the user, BCA is the bone salt amount as measured by DXA method. DXA means "Dual Energy X-ray Absorptiometry". DXA method is popular method for measurement of bone salt amount or bone density which has been used in the today hospitals in which two different X-ray beams are irradiated to the patient to be detected, and the beams passing through the body are detected so as to measure the bone salt amount or bone density.

Figure 22:
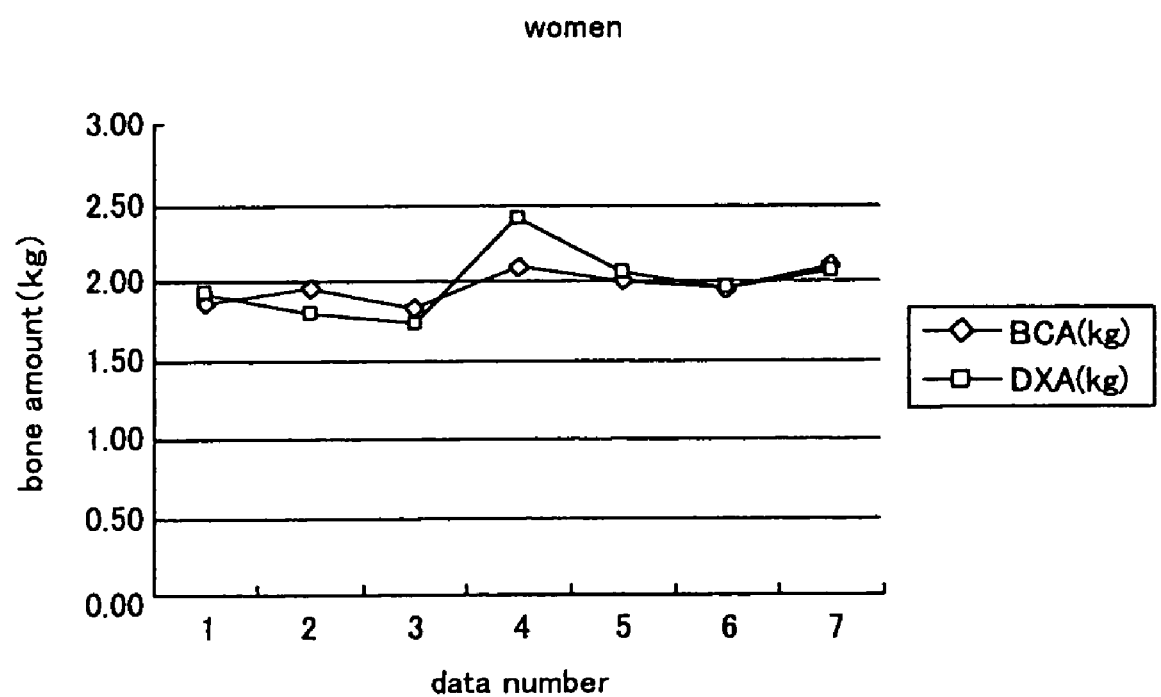
FIG. 22 is a view illustrating graphically the difference of the bone amounts as measured by BCA method and DXA method of FIG. 20.

FIGS. 21 and 22 are the line graphs for comparing the measured bone weights as respectively shown in Table of FIGS. 19 and 20. In view of those graphs, the bone calcium amount (BCA) which has been calculated as above mentioned will be enough to be the same as the BCA as measured by DXA method.

The resulting approximate bone weight which has been calculated by multiplying a certain constant to the weight excluding the fat weight, as estimated on the basis of the measured impedance can be corrected by reviewing the length around the wrist and length around the ankle as the personal information, but the bone weight can be estimated on the basis of the length around the wrist and length around the ankle, and then this result can be corrected by reviewing the body weight excluding the fat weight and the personal information so as to get the further corrected value of the bone weight.

The display equipment of the present invention for indication of the bone weight, water content and muscle weight of the body is to measure the bone weight, water content and muscle weight of the body or the fat amount of the body, so as to analyze the components of the body thereby to indicate them so that it can be used for monitoring and managing his body condition during diet time and exercise time. Further, the indication or instructions can be done by audio media. In the other wording, the bone weight, water content and/or muscular weight and the fat ratio as represented on the display equipment may be informed by voice.

Further, it can inform some warning such as "water content is being reduced, and then, drink water or . . . ", "the muscular weight is being lowered, and then, exercise everyday . . . times".

The display as used for the inventive equipment can be combined with an aero-bicycle meter so as to provide an indicator for the exercise, and further, can be combined with a weight meter so as to provide the presentation of the data such as bone weight, water content and/or muscle weight or fat amount, and fat ratio. Further, it can be combined with a step counter, so as to provide the monitoring data such as bone weight, water content and/or muscle weight of the user during the walking time.

The display equipment of the present invention can not be restricted within the above described embodiment, and further can be modified and changed within the scope as recited by the attached claims. For example, the inventive equipment can be provided with any somatotype of the body detectors such as a weighting meter, a fat detector, a measure of body length and the like. Further, the inventive display equipment could be combined with any of exercise machine such as an aero-bicycle, a room runner and a step walker that are to be used indoor.

INDUSTRIAL APPLICABILITY

As explained above, the display equipment in accordance with the present invention can measure the approximate values of the bone amount, water content and/or muscular ratio of the human body so as to provide the result of the measurements so that such numerical value would be proposed so as to give healthy diet condition to the user at the same time to manage the health condition of the body.

What is claimed is:

1. A display equipment, comprising:
   a belt configured to wrap a body, a plurality of electrodes being mounted on the belt, the plurality of electrodes configured to contact a surface of the body;
   a measuring unit configured to measure impedance of the body by feeding a measuring current through the plurality of the electrodes into the body;
   a memory configured to store personal information including at least one of gender, age, height, body weight, length around the wrist, and length around the hand of the body;
   a calculating unit configured to calculate bone weight of the body on the basis of the measured impedance and the stored personal information;
   a judging unit configured to judge a somatotype of the body, the somatotype being classified on the basis of a correlation between the calculated bone weight and the body weight; and
   a display configured to display the somatotype judged by the judging unit.

2. The display equipment for as set forth in claim 1, wherein the personal information includes at least one of gender, age, and the combination thereof.

3. The display equipment as set forth in claim 1, further comprising:
   a feeding unit configured to feed a pulsed current through the plurality of electrodes into the body, so as to treat the body.

4. The display equipment as set forth in claim 1, wherein the calculating unit calculates the bone weight and muscular weight of the body on the basis of the impedance and the personal information;
   the judging unit judges the somatotype of the body and a first additional somatotype of the body, the first additional somatotype being classified on the basis of a correlation between the calculated muscular weight and the body weight; and
   the display displays the somatotype and the first additional somatotype judged by the judging unit.

5. The display equipment as set forth in claim 1, wherein the calculating unit calculates the bone weight and water weight of the body on the basis of the impedance and the personal information;
   the judging unit judges the somatotype of the body and a second additional somatotype of the body, the second additional somatotype being classified on the basis of a correlation between the calculated water weight and the body weight; and
   the display displays the somatotype and the second additional somatotype judged by the judging unit.

* * * * *

UNITED STATES PATENT AND TRADEMARK OFFICE
CERTIFICATE OF CORRECTION

| | | |
|---|---|---|
| PATENT NO. | : 7,764,991 B2 | Page 1 of 1 |
| APPLICATION NO. | : 10/517490 | |
| DATED | : July 27, 2010 | |
| INVENTOR(S) | : Yamazaki et al. | |

It is certified that error appears in the above-identified patent and that said Letters Patent is hereby corrected as shown below:

Claim 2, column 16, line 31, change "equipment for" to --equipment--.

Signed and Sealed this

Second Day of November, 2010

David J. Kappos
*Director of the United States Patent and Trademark Office*